(12) United States Patent
Traynelis et al.

(10) Patent No.: US 8,906,067 B2
(45) Date of Patent: Dec. 9, 2014

(54) POSTERIOR INCREMENTAL SPINAL FIXATION SYSTEM

(75) Inventors: Vincent C. Traynelis, Chicago, IL (US); Gregory Marik, Collierville, TN (US); Bradley Coates, Yarmouth, IA (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

(21) Appl. No.: 13/426,184

(22) Filed: Mar. 21, 2012

(65) Prior Publication Data
US 2013/0253588 A1   Sep. 26, 2013

(51) Int. Cl.
*A61B 17/70* (2006.01)
(52) U.S. Cl.
USPC .......................... 606/265; 606/261; 606/264
(58) Field of Classification Search
USPC .............. 606/246, 250–279, 300–321
See application file for complete search history.

(56) References Cited

U.S. PATENT DOCUMENTS

| 7,645,294 | B2* | 1/2010 | Kalfas et al. ............... 606/250 |
| 8,016,861 | B2* | 9/2011 | Mitchell et al. ............ 606/264 |
| 8,430,913 | B2* | 4/2013 | James et al. ................ 606/264 |
| 2010/0324599 | A1* | 12/2010 | Montello et al. ............ 606/264 |

* cited by examiner

*Primary Examiner* — Mary Hoffman
*Assistant Examiner* — Christina Negrellirodrigue
(74) *Attorney, Agent, or Firm* — Sorell, Lenna & Schmidt, LLP

(57) ABSTRACT

A spinal fixation device may include a bone anchoring member, a rod receiver, and an connection member. The rod receiver may include a channel for receiving a rod projection from a first adjacent fixation assembly. The rod receiver may have a central axis such that the channel is generally perpendicular to the central axis. The connection member may have a rod projection configured to extend to a second adjacent fixation assembly. The rod receiver may be coupled to the connection member and rotatable about the central axis of the rod receiver. The interior fixation assembly may be axially fixed such that the bone anchoring member, the rod receiver and the connection member are not translatably movable relative to each other.

20 Claims, 9 Drawing Sheets

POSTERIOR INCREMENTAL SPINAL FIXATION SYSTEM

FIELD OF INVENTION

Embodiments of the invention relate to multi-level spinal fixation systems. More particularly, the embodiments relate to spinal fixation constructs having bone anchors at each level and rods spanning the levels.

BACKGROUND

The spinal column is a biomechanical structure composed primarily of support structures including vertebrae and intervertebral discs and soft tissue structures for motive and stabilizing forces including muscles and ligaments. The biomechanical functions of the spinal column include support, spinal cord protection, and motion control between the head, trunk, arms, pelvis, and legs. These biomechanical functions may require oppositely designed structures. For example, the support function may be best addressed with rigid load bearing structures while motion control may be best suited for structures that are easily movable relative to each other. The trade-offs between these biomechanical functions may be seen within the structures that make up the spinal column. Damage to one or more components of the spinal column, such as an intervertebral disc, may result from disease or trauma and cause instability of the spinal column and damage multiple biomechanical functions of the spinal column. To prevent further damage and overcome some of the symptoms resulting from a damaged spinal column, a spinal fixation device may be installed to stabilize the spinal column. Furthermore, the damage may extend between more than two vertebrae (levels). Damage across multiple levels requires spinal constructs that may span across those levels.

The damage that occurs in the spine may not be homogenous through a vertebra. Portions of the vertebra may be better suited to provide support for a spinal fixation construct. Traditionally, spinal constructs have used a single rod to extend the length of the construct. Thus, when a multi-level construct is implanted, the placement of the bone anchors is at least partially limited by the shape of the rod. Either a surgeon must bend a rod to fit within the bone anchoring members across the spinal levels, or the surgeon must try to place the screws along a relatively linear path along the length of the construct which may not be the best choice based on the underlying bone.

Spinal surgeries may also correct deformities in the spine. Such surgeries involve manipulating vertebra to move the curves of the spine inline. In prior art systems, spinal manipulations occur along the entire construct, necessitated by the spinal rod extending along the entirety of the spinal construct. Generally, the manipulation begins with capturing the rod near the ends and working toward the middle of the construct. The rod is captured along the length in adjacent levels as the vertebra in the central portions of the vertebral column is captured. Such systems require manipulation of the rod as well as manipulation of the vertebral segments along the length.

The description herein of problems and disadvantages of known apparatuses, methods, and devices is not intended to limit the invention to the exclusion of these known entities. Indeed, embodiments of the invention may include, as a part of the embodiment, portions or all of one or more of the known apparatus, methods, and devices without suffering from the disadvantages and problems noted herein.

SUMMARY OF ASPECTS OF THE INVENTION

An embodiment of the invention may include a spinal fixation system comprising an interior fixation assembly, an open fixation assembly and an end fixation assembly. The interior fixation assembly may include a bone anchoring member, a rod. receiver, and an connection member. The rod receiver may include a channel for receiving a rod projection from a first adjacent fixation assembly. The rod receiver may have a central axis such that the channel is generally perpendicular to the central axis. The connection member may have a rod projection configured to extend to a second adjacent fixation assembly. The rod receiver may be coupled to the connection member and rotatable about the central axis of the rod receiver. The interior fixation assembly may be axially fixed such that the bone anchoring member, the rod receiver and the connection member are not translatably movable relative to each other. The end fixation assembly may include a bone anchoring member and a rod receiver axially fixed to the bone anchoring member. The rod receiver may be configured to receive the bone extending member from the interior fixation assembly. The open fixation assembly may comprise a bone anchoring member and an connection member. The connection member may have a rod projection configured to be received in the rod receiver of the interior fixation assembly. The rod projections of the interior fixation device and the open fixation device are angularly offset from one another.

Another embodiment of the invention provides a spinal fixation device including a bone anchoring member, a rod receiver, and a connection member. The rod receiver may include a channel for receiving a rod projection from a first adjacent fixation assembly. The rod receiver may have a central axis such that the channel is generally perpendicular to the central axis. The connection member may have a rod projection configured to extend to a second adjacent fixation assembly. The rod receiver may be coupled to the connection member and rotatable about the central axis of the rod receiver. The interior fixation assembly may be axially fixed such that the bone anchoring member, the rod receiver and the connection member are not translatably movable relative to each other.

Yet another embodiment may include a method for implanting a spinal fixation system. A step may include attaching a first spinal fixation device to a first vertebra. Another step includes attaching a second spinal fixation device to a second vertebra. A third spinal fixation device may be attached to a third vertebra. A step may provide rotating a first rod projection about a central axis of the first spinal fixation device such that the rod projection extends toward the second spinal fixation device. Yet another step may provide capturing the first rod projection in a channel on the second spinal fixation device. A second rod projection may be rotated about a central axis of the second spinal fixation device such that the rod projection extends toward the third spinal fixation device after the first rod projection is captured in the receiver of the second spinal fixation device. Another step may capture the second rod projection in a channel on the third spinal fixation device.

Additional aspects and features of the present disclosure will be apparent from the detailed description and claims as set forth below.

DETAILED DESCRIPTION

Figure 1:
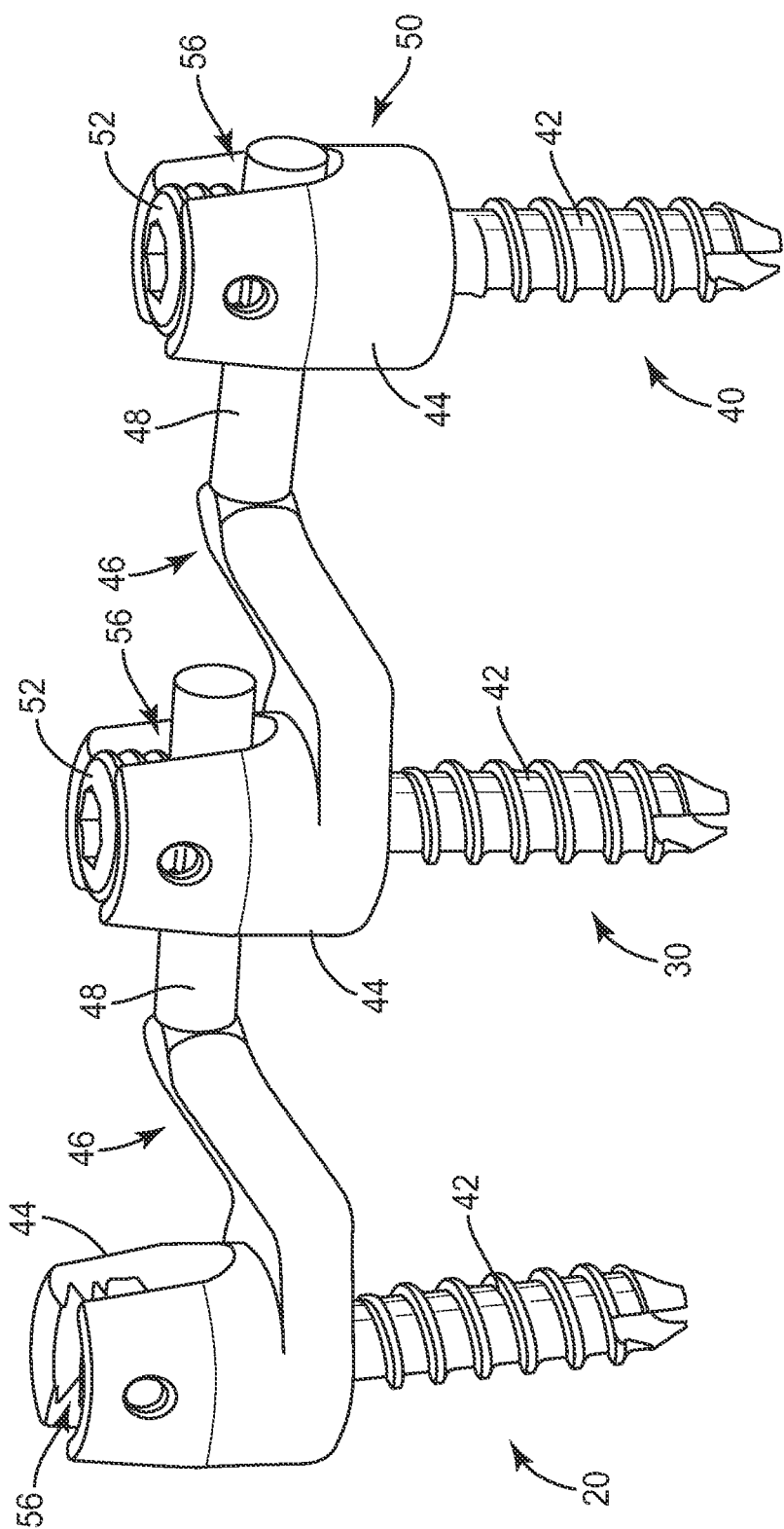
FIG. 1 is a view of a posterior incremental spinal fixation system according to an embodiment of the present invention.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Turning now to FIG. 1, FIG. 1 is a view of a posterior incremental spinal fixation system 10 according to an embodiment of the present invention. The spinal fixation system 10 includes an open screw assembly 20, an interior screw assembly 30 and an end screw assembly 40. Assemblies 20, 30 and 40 each have a bone screw 42. Interior assembly 30 and open assembly 20 each have a receiver 44 and a connection member 46 with a rod projection 48. End assembly 40 has an end receiver 50. Interior receiver 30 and end receiver 40 each have a set screw 52.

The fixation assemblies 20, 30 and 40 together form the fixation system 10. While the assemblies 20, 30 and 40 have been shown with bone screws 42, other bone fixation elements such as hooks may be used to fix the assemblies to bone. Preferably, each fixation assembly will be placed in adjacent levels of vertebra along the spinal column. The orientation between the receivers 44 and 50 and the bone screws 42 may be multi-axis. The screw 42, then, may angle relative to the receivers 44 and 50. Other embodiments may include fixed axis screws where the receiver 44 or 50 is aligned axially with the bone screw 42 or fixed at an angle relative to the bone screw 42. The receiver 44 couples to the connection member 46 to capture the screw 42 in the assemblies 20 and 30. Because the end receiver 50 does not have a connection member 46, the receiver 50 captures the screw 42 only and does not fix a connecting member to the assembly.

The open assembly 20 in the present embodiment includes a channel 56. Each of the receivers 44 and 50 include a channel. For the open assembly 20, the channel 56 does not receive a rod projection from an adjacent level. Thus, the channel 56 is not required in the open receiver 20. However, it may be desirable to include a channel 56 in the spinal system 10 so that an adjacent level may be included in the spinal system 10 (for example, as part of a revision or if the surgeon chooses to extend the spinal construct 10 through the open receiver 20.) If the open assembly 20 includes a channel 56, then the assembly may also include a plug to fix the receiver 44 to the bone screw 42. The plug may be similar to a set screw, but extend far enough into the receiver 44 to fix relative movement of the screw 42 to the receiver 44.

The interior assembly 30 includes a channel 56 for receiving the rod projection 48 from the open assembly 20. The set screw 52 captures the rod projection 48 of the open assembly 20. The connection member 46 of the interior assembly 30 projects toward the end assembly 40. Because the connection member 46 and the receiver 44 are rotatable relative to each other, the channel 56 in the receiver 44 can be oriented without fixing the connection member 46 of the interior assembly 30.

The end assembly 40 includes a receiver 50 that has a channel 56 extending through it. The channel receives the rod projection 48 of the connection member 46 of the interior assembly 30. The channel 56 of the end assembly 40 can be oriented to receive the rod projection 48. The set screw 52 captures the rod projection 48 in the channel 56. The end assembly 40, then, couples the last rod projection 48 to fix the spinal fixation system 10 between the last two levels. The spinal fixation system 10 may incrementally fix multiple levels without being restrained by prior level fixation.

The connection member 46 is rotationally adjustable to the receiver 44. The rotatability of the channel 56 relative to the connection member 46 allows for rod projections 48 to be angularly offset from each other at the same level. Thus, a rod projection 48 coupled to an interior assembly 30 may be angularly offset from the rod projection 48 extending from the interior assembly 30. In prior art systems, such angular offsets are not possible without manipulation of the rod. Even when the rod is manipulated (bent), the amount of bending is limited and may structurally weaken the rod.

The connection member 46 may also attach to other orthopedic devices. For example, the connection member 46 may be modified to connect to an intraspinous device such as an artificial disk or cage. Alternatively, the connection member 46 may be configured to connect to an assembly at the facet joint. Such choices are possible because the system of the present invention allows for individual level-by-level choice for the entire construct.

The rod projections 48 may be laterally offset from the assembly 20 or 30 by the connection member 46. Additionally, the connection member 46 may have a height offset to raise the rod projection to a level in line with the channel 56 in the assemblies 30 or 40. The lateral offset allows the connection member to span the intervertebral space and the height offset increases contact between the channel 56 and the set screw 52 to the rod projection 48. When the set screws 52 are tightened to the rod projections 48, the spinal fixation system 10 is stably secured between the open assembly 20 and the end assembly 40.

Figure 2:
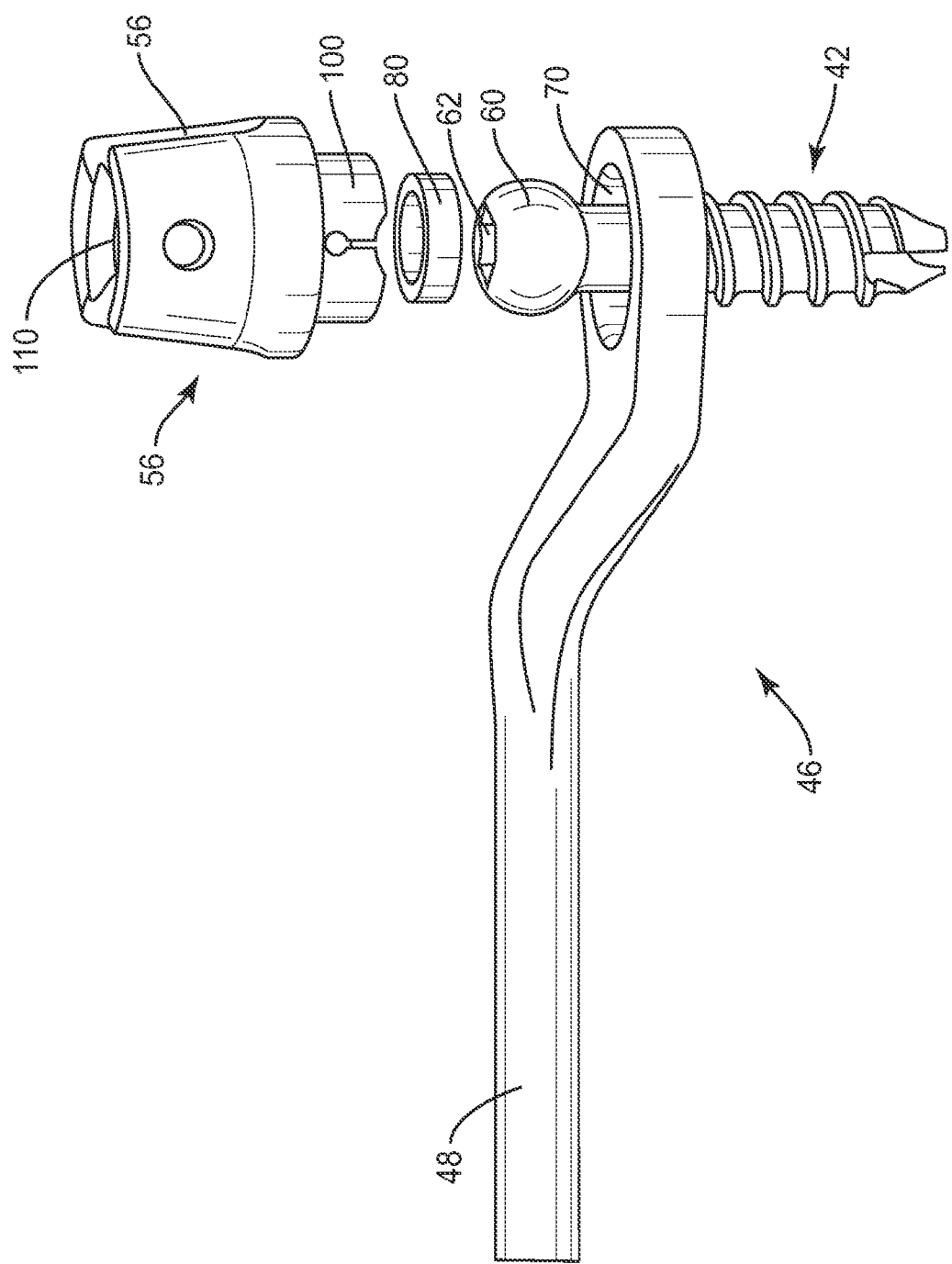
FIG. 2 is an exploded view of the spinal fixation system of FIG. 1.

Turning now to FIG. 2, FIG. 2 is an exploded view of the spinal fixation system 10 of FIG. 1. The bone anchoring member 42 includes a head 60. The head 60 has a tool recess 62 so that the bone anchoring member 42 may be implanted in bone. A seat recess 70 on the connection member 46 seats the head 60 of the bone anchoring member 42 between a crown 80 and flanges 100 of the receiver 50. The seat recess 70 collapses the flanges 100 of the receiver 50 against the underside of the head 60 of the bone anchoring member 42.

An upper side of the crown 80 may extend into the channel 56 of the receiver 50. When the rod projection is received in the channel 56, the rod projection may collapse the crown 80 against the head 60 of the bone anchoring member 42. The crown 80 then fixes the receiver 50 to the connection member 46 by further compressing the flanges 100 against the head 60 and the seat recess 70.

Threads 110 on the receiver 50 receive the set screw. The set screw, then, may be advanced against the rod projection to compress the crown 80 against the head 60. As the rod projection is fixed in place by the advancing set screw, the orientation of the channel 56 and the rod projection 48 extending from the assembly 30 is also fixed. Thus, the surgeon must orient the rod projection 48 as the set screw is tightened to ensure proper orientation for the rod projection 498 to the adjacent assembly.

Figure 3:
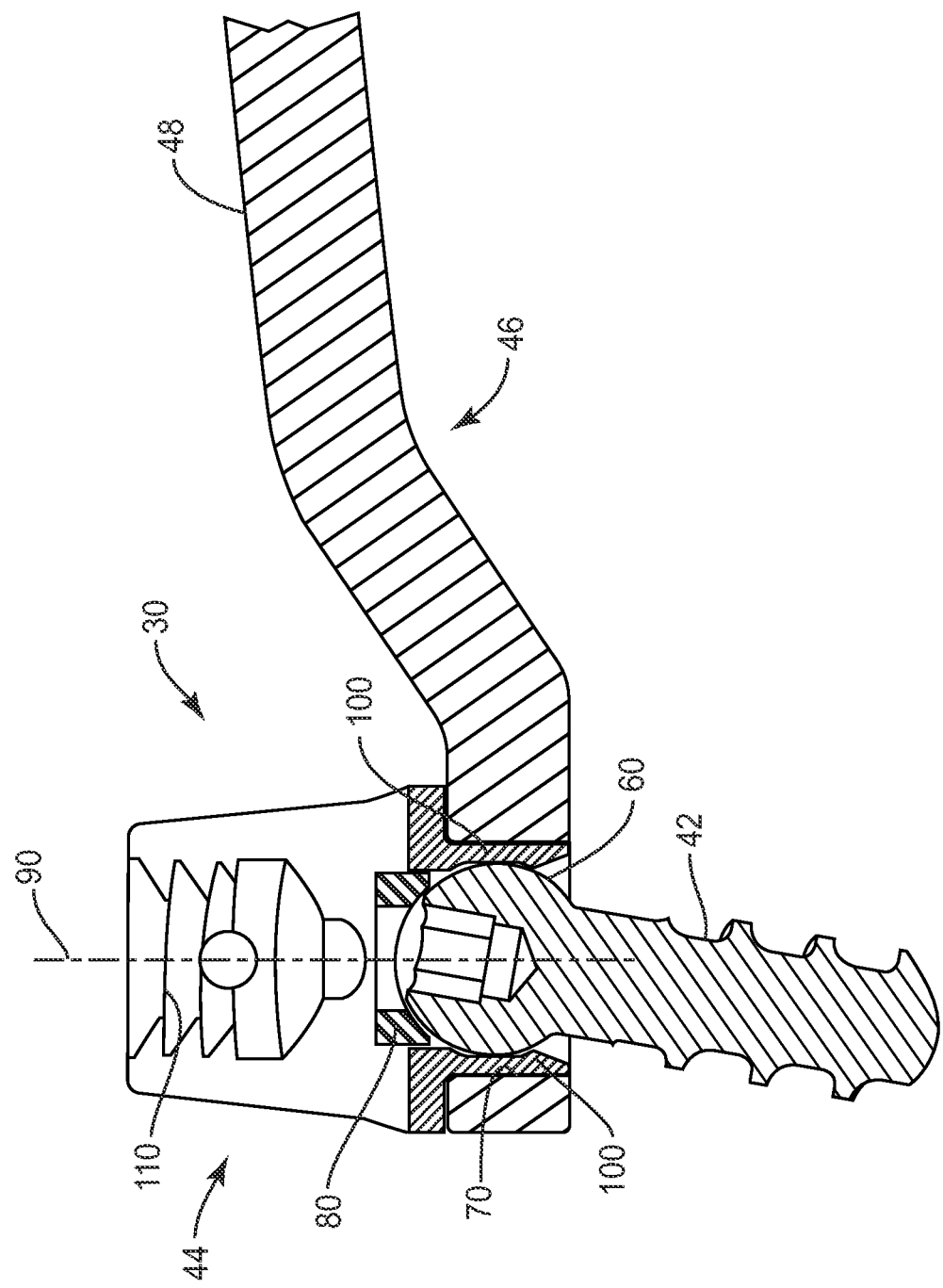
FIG. 3 is a cross sectional view of an interior fixation assembly of the spinal fixation system of FIG. 1.

Turning now to FIG. 3, FIG. 3 is a cross sectional view of the interior fixation assembly 30 of the spinal fixation system 10 of FIG. 1. The receiver 44, crown 80, connection member 46 and the bone anchoring member 42 are generally aligned along a central axis 90 of the assembly 30. The bone anchoring member 42 may be rotatable within the seat recess 70 such that a cone of possible orientations of the bone anchoring member 42 extends about the central axis 90.

Figure 4:
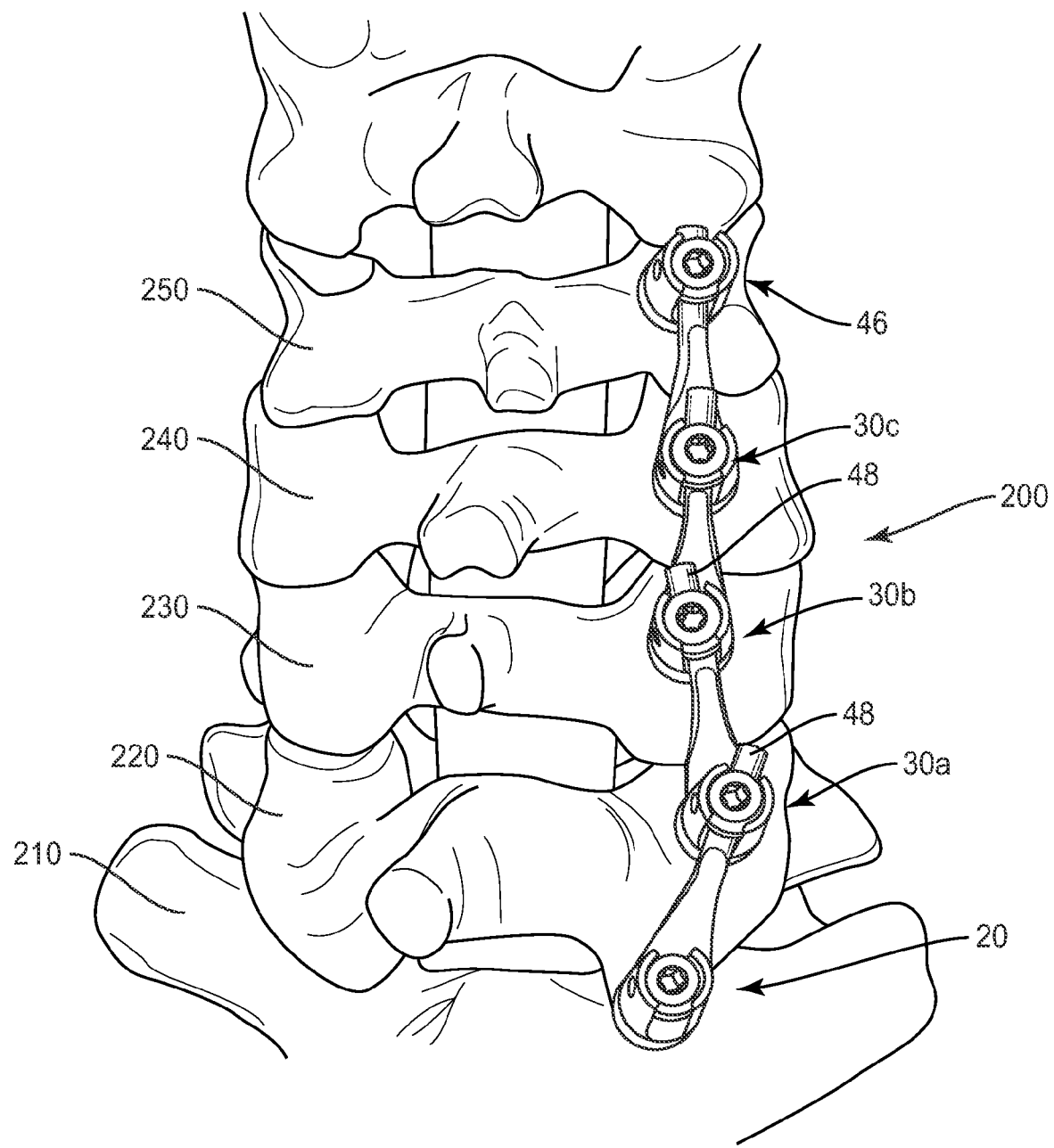
FIG. 4 is a posterior view of a spinal fixation system implanted in a spinal column and including elements of the spinal fixation system 10 of FIG. 1.
Figure 5:
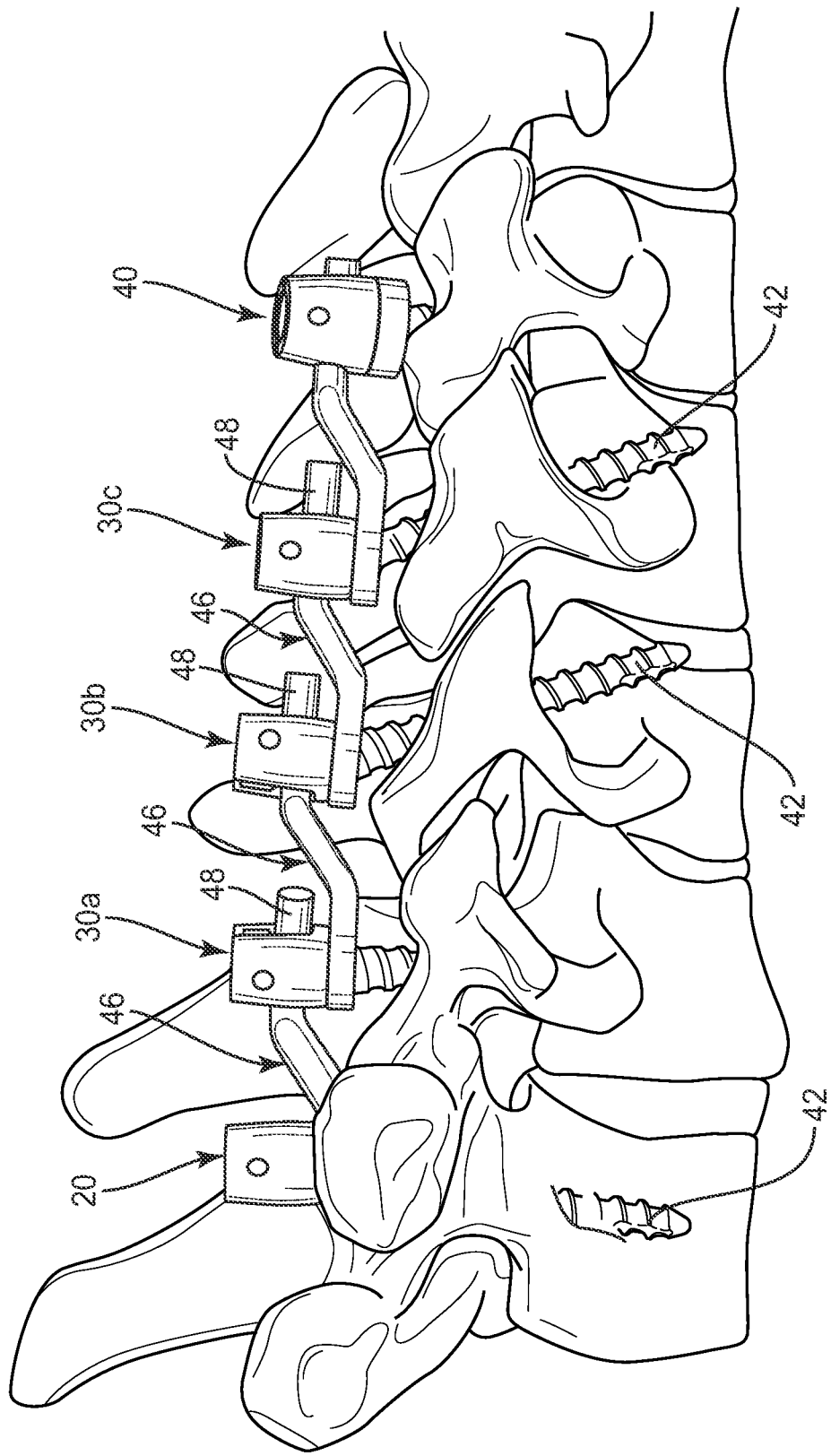
FIG. 5 is a lateral view of the spinal fixation system shown in FIG. 4.

Turning now to FIGS. 4 and 5, FIG. 4 is a posterior view of a spinal fixation system 200 implanted in a spinal column and including elements of the spinal fixation system 10 of FIG. 1. FIG. 5 is a lateral view of the spinal fixation system 200 shown in FIG. 4. The system 200 includes 5 levels spanning a first, second, third, fourth and fifth vertebra 210, 220, 230, 240 and 250, respectively. The spinal fixation system 200 includes an open assembly 20, an end assembly 40, and 3 interior connectors 30a, 30b, and 30c. The open assembly 20, interior assemblies 30a, 30b, and 30c, and the end assembly 40 are implanted in the first, second, third, fourth and fifth vertebrae 210-250, respectively. While the open assembly 20 was placed at the first vertebra 210, another embodiment would allow the open assembly 20 to be placed at the fifth vertebra 250 and thus the interior assemblies 30a-30c and the end assembly 40 would extend from the fourth vertebra 240 down to the first vertebra 210. Additionally, while this spinal system 200 includes 5 levels, fewer or more levels may be included to create constructs appropriate for the surgery.

The system 200 shows the relative angular offset that may be achieved between adjacent assemblies. The rod projection 48 of the open assembly 20 is received in a first orientation on the first interior assembly 30a. The rod projection 48 of the first interior assembly 30a is rotated relative to the rod projection 48 of the open assembly 20. Other adjacent rod projections may be more linearly aligned from assembly to assembly, but the functionality of the relatively rotatable rod projections 48 allows for a fixation assembly (in this case assembly 30a) to be offset laterally away from the midline of the vertebral column relative to the other assemblies in the spinal fixation system 200. For example, if the bone in the second vertebra 220 is such that the assembly 30a is required to be more laterally placed in the vertebra 220, then the ability of the rod projections 48 to be angularly oriented at the assemblies allows for placement of assemblies without restrictions of the placement of assemblies at adjacent levels.

As shown in FIG. 5, the bone anchoring elements 42 may extend from the receivers in orientations about the central axis of the assemblies. The height offsets of the connection members 46 place the rod projections 48 level with channels of the receivers to maximize contact between the channels and set screws to the rod projections 48.

Figure 6:
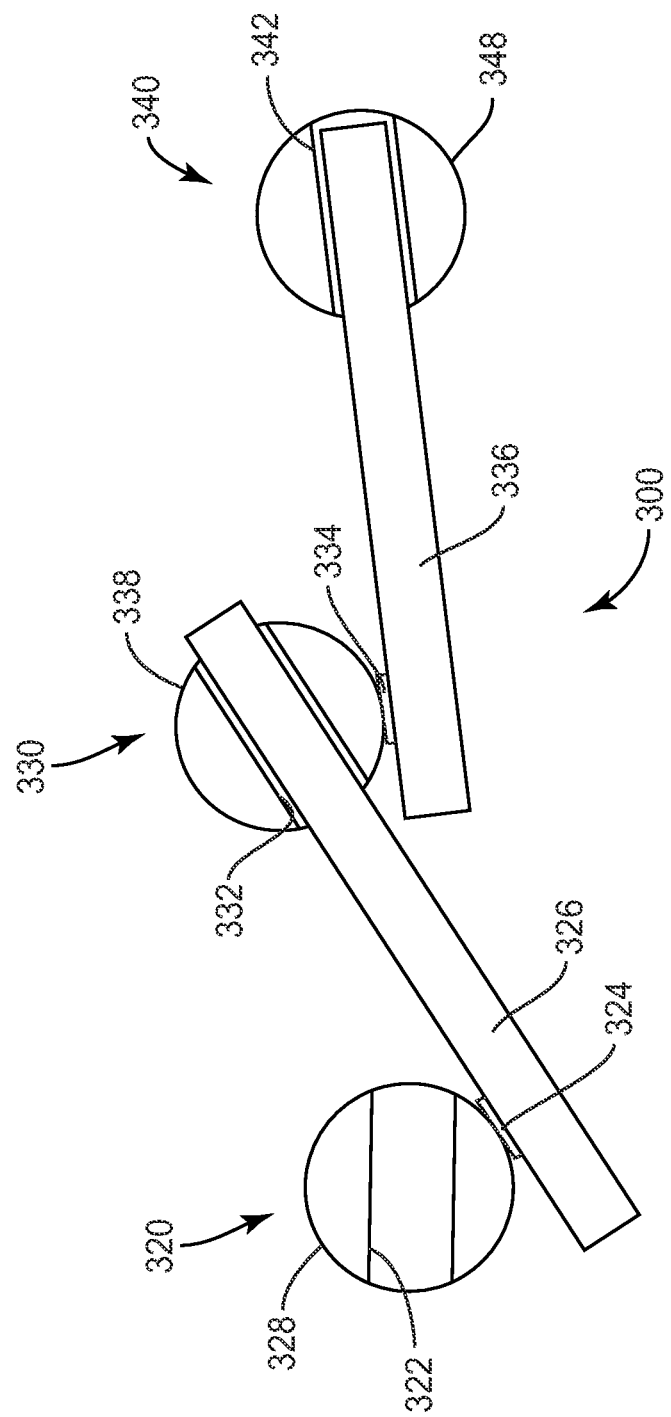
FIG. 6 is another embodiment of a posterior incremental spinal fixation system according to an embodiment of the present invention.

Turning now to FIG. 6, FIG. 6 is another embodiment of a posterior incremental spinal fixation system 300 according to an embodiment of the present invention. The spinal fixation system 300 includes an open fixation assembly 320, an interior fixation assembly 330 and an end fixation assembly 340.

The open fixation assembly 320 includes a channel 322 and a pin 324 which couples a rod projection 326 to a receiver 328. Similarly, the interior fixation assembly 330 includes a channel 332 and a pin 334 which couples a rod projection 336 to a receiver 338. The end assembly 340 includes a channel 342 and a receiver 348. The pins 324 and 334 may be on a ring rotatable around the receiver 328 and 338 respectively. Similar to previous embodiments, the rod projections 326 and 336 may be angularly oriented with respect to the channels 322 and 332.

Figure 7:
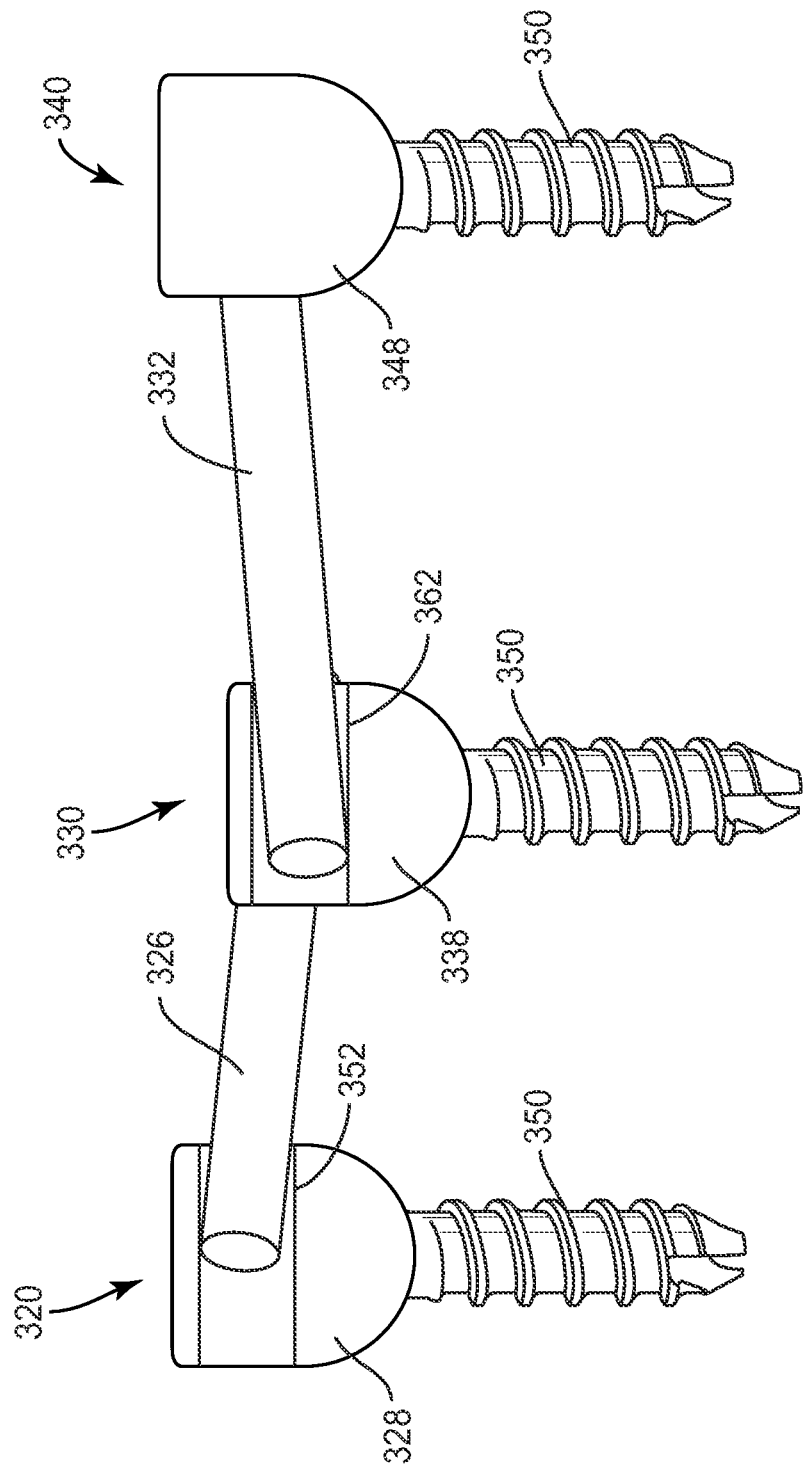
FIG. 7 is a lateral view of the spinal fixation system of FIG. 6.

Turning now to FIG. 7, FIG. 7 is a lateral view of the spinal fixation system 300 of FIG. 6. Bone anchoring members 350 extend from the receivers 328, 338, and 348. Rings 352 and 362 may rotate the pins around the outer circumference of the receivers 328 and 338. The pins may allow height adjustment at the ends of the rod projections 326 and 338 by rotating the members 326 and 336 relative to the receivers 328 and 338.

Figure 8:
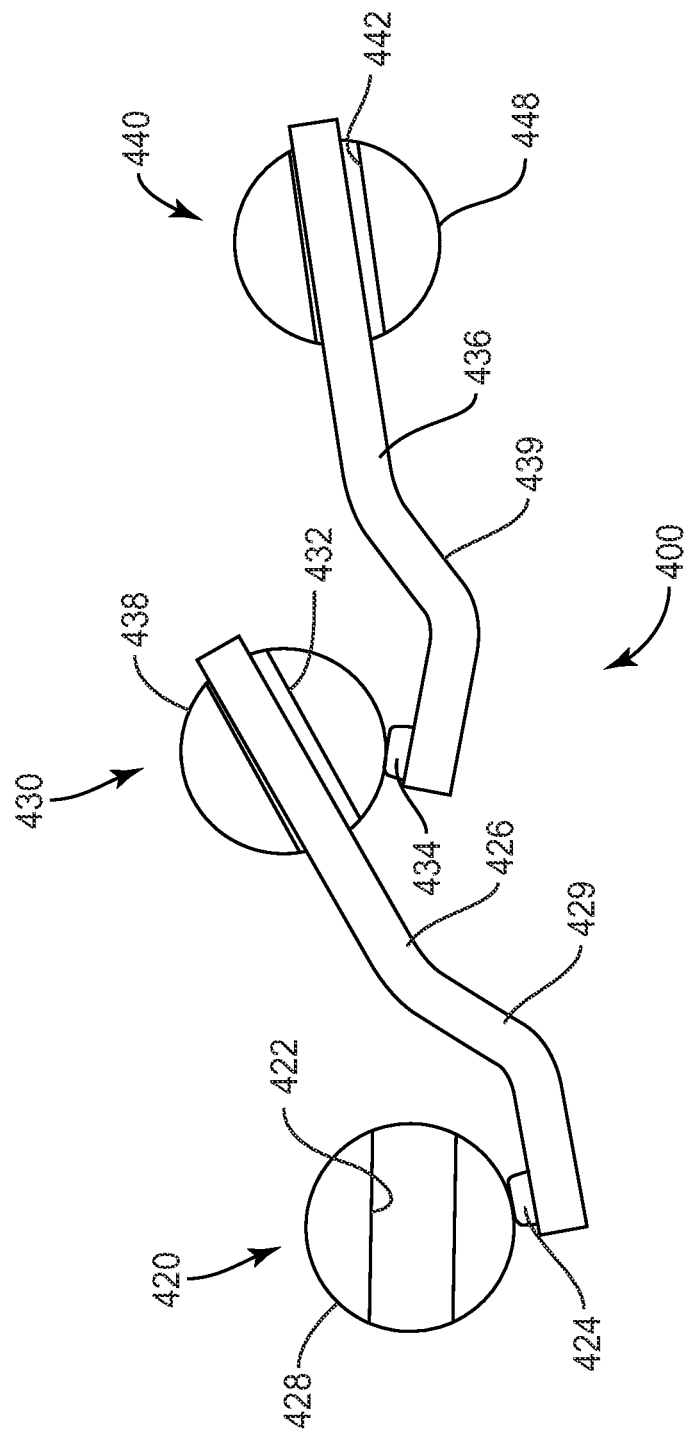
FIG. 8 is a posterior view of another embodiment of a posterior incremental spinal fixation system according to an embodiment of the present invention.

Turning now to FIG. 8, FIG. 8 is a posterior view of another embodiment of a posterior incremental spinal fixation system 400 according to an embodiment of the present invention. The spinal fixation system 400 includes an open fixation assembly 420, an interior fixation assembly 430 and an end fixation assembly 440. The open fixation assembly 420 includes a channel 422 and a pin 424 which couples a rod projection 426 to a receiver 428. Similarly, the interior fixation assembly 430 includes a channel 432 and a pin 434 which couples a rod projection 436 to a receiver 438. The end assembly 440 includes a channel 442 and a receiver 448. A medial offset 429 may orient the rod projection 426 into the channel 432. Similarly, a medial offset 439 may orient the rod projection 436 into the channel 442. The pins 424 and 434 may be on a ring rotatable around the receiver 428 and 438 respectively. Similar to previous embodiments, the rod projections 426 and 436 may be angularly oriented with respect to the channels 422 and 432.

Figure 9:
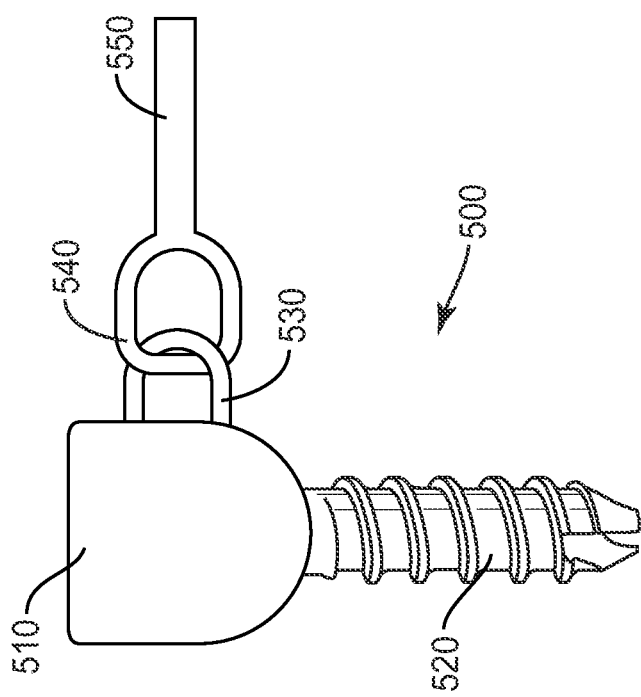
FIG. 9 is a lateral view of another embodiment of a spinal fixation assembly according to an embodiment of the present invention.

Turning now to FIG. 9, FIG. 9 is a lateral view of another embodiment of a spinal fixation assembly 500 according to an embodiment of the present invention. The fixation assembly 500 includes a receiver 510, a bone anchoring member 520, a yoke 530, a pinion 540 and a rod projection 550. The assembly 500 may radially orient the rod projection 550 relative to the receiver 510 through the yoke 530 and pinion 540. The yoke 530 may extend around the circumference of the receiver 510. The pinion may create a height offset of the rod projection 550 for connection to an adjacent assembly. When the rod projection 550 is fixed to the adjacent level, the yoke 530 and pinion 540 are stabilized within a spinal system. In such an embodiment, the receiver 510 may be a single piece without a rotatable connection member coupled to the receiver 510. The yoke and pinion orientation allows for rotatable orientations between the receiver 510 and rod projection 550.

The foregoing detailed description is provided to describe the invention in detail, and is not intended to limit the invention. Those skilled in the art will appreciate that various modifications may be made to the invention without departing significantly from the spirit and scope thereof.

Furthermore, as used herein, the terms components and modules may be interchanged, it is understood that all spatial references are for illustrative purposes only and can be varied within the scope of the disclosure.

The invention claimed is:

1. A spinal fixation system, comprising: an interior fixation assembly, comprising:
   a bone anchoring member;
   a rod receiver comprising a channel for receiving a rod projection from a first adjacent fixation assembly, the rod receiver having a central axis and the channel being generally perpendicular to the central axis; and a connection member having a rod projection configured to extend to a second adjacent fixation assembly, the rod receiver being coupled to the connection member and rotatable about the central axis of the rod receiver, the interior fixation assembly being axially fixed such that the bone anchoring member, the rod receiver and the connection member are not translatably movable relative to each other;

an end fixation assembly comprising a bone anchoring member and a rod receiver axially fixed to the bone anchoring member, the rod receiver being configured to receive the bone extending member from the interior fixation assembly; and an open fixation assembly comprising a bone anchoring member and a connection member, the connection member having a rod projection configured to be received in the rod receiver of the interior fixation assembly, wherein the rod projections of the interior fixation device and the open fixation device are angularly offset from one another.

2. The spinal fixation system of claim 1, further comprising a plurality of interior fixation assemblies, a first interior fixation assembly configured to receive the rod projection of the open fixation assembly, the end fixation assembly being configured to receive the rod projection of a second interior fixation assembly.

3. The spinal fixation system of claim 1, wherein the interior fixation assembly is a multi-axial fixation assembly configured to allow a plurality of angular orientations between the rod receiver and the bone anchoring member.

4. The spinal fixation system of claim 1, wherein the bone anchoring member of at least one of the interior fixation assembly, end fixation assembly and open fixation assembly is a screw.

5. The spinal fixation system of claim 4, further comprising a set screw configured to capture the rod projection of the open fixation assembly to the rod receiver of the interior fixation assembly.

6. The spinal fixation system of claim 5, wherein the rod receiver further comprises a plurality of flanges configured to couple to a head of the screw, the connection member having a seat recess configured to receive the flanges of the rod receiver.

7. The spinal fixation system of claim 1, wherein the connection member extends away from the rod receiver, the rod projection connecting to the portion of the connection member extended away from the rod receiver, the connection member further including a height offset such that the rod projection is generally at the same height as the channel of the rod receiver.

8. The spinal fixation system of claim 1, wherein the connection member is pinned to the receiver member, the connection member being rotatable about the pin.

9. The spinal fixation system of claim 1, wherein the connection member is coupled to the receiver by a yoke and pinion connector.

10. A spinal fixation device, comprising:
a bone anchoring member;
a rod receiver comprising a channel having a pair of upright arms for receiving a rod projection, the rod receiver having a central axis and the channel being generally perpendicular to the central axis;
a connection member comprising a seat recess having a head of the bone anchoring member disposed therein, the connection member having a rod projection configured to extend to a second adjacent fixation device, a portion of the rod receiver being disposed in the seat recess such that the rod receiver is rotatable about the central axis of the rod receiver, the spinal fixation device being axially fixed such that the bone anchoring member, the rod receiver and the connection member are not translatably movable relative to each other along the central axis, and a set screw engaged to the pair of upright arms and configured to lock the rod receiver such that when the set screw is fully engaged in the upright arms, the rod receiver is not rotatably adjustable to the connection member.

11. The spinal fixation device of claim 10, wherein the spinal fixation device is a multi-axial fixation assembly configured to allow a plurality of angular orientations between the rod receiver and the bone anchoring member.

12. The spinal fixation device of claim 10, wherein the bone anchoring member of the spinal fixation device is a screw.

13. The spinal fixation device of claim 12, wherein the set screw is configured to capture a rod projection of another spinal fixation device to the rod receiver of the spinal fixation device.

14. The spinal fixation device of claim 13, wherein the portion of the rod receiver comprises a plurality of flanges configured to couple to the head.

15. The spinal fixation device of claim 10, wherein the connection member extends away from the rod receiver, the rod projection connecting to the portion of the connection member extended away from the rod receiver, the connection member further including a height offset such that the rod projection is generally at the same height as the channel of the rod receiver.

16. The spinal fixation device of claim 10, wherein the rod portion has a cylindrical cross sectional configuration.

17. A method for implanting a spinal fixation system, comprising the steps of:
 i. attaching a first spinal fixation device to a first vertebra;
 ii. attaching a second spinal fixation device to a second vertebra;
 iii. attaching a third spinal fixation device to a third vertebra;
 iv. rotating a first rod projection about a central axis of the first spinal fixation device such that the rod projection extends toward the second spinal fixation device;
 v. capturing the first rod projection in a channel on the second spinal fixation device;
 vi. rotating a second rod projection about a central axis of the second spinal fixation device such that the rod projection extends toward the third spinal fixation device after the first rod projection is captured in the receiver of the second spinal fixation device; and
 vii. capturing the second rod projection in a channel on the third spinal fixation device.

18. The method of claim 17, wherein the first rod projection and the second rod projection are angularly offset from one another.

19. The method of claim 18, wherein the rod projections of the first and second spinal fixation devices are captured by a set screw.

20. A spinal fixation system, comprising:
the spinal fixation device of claim 10; and
the second adjacent fixation device, the second adjacent fixation device comprising:
 a second bone anchoring member,
 a second rod receiver comprising a second channel having a pair of upright arms for receiving the rod projection such that an outer surface of the rod projection engages an inner surface of the second channel.

* * * * *